(12) United States Patent
Arm et al.

(10) Patent No.: US 9,526,821 B2
(45) Date of Patent: Dec. 27, 2016

(54) BLOOD SEPARATION AND CONCENTRATION SYSTEM

(71) Applicant: Biomet Biologics, LLC, Warsaw, IN (US)

(72) Inventors: Douglas M. Arm, Mission Viejo, CA (US); Michael Ponticiello, Mission Viejo, CA (US); Surinder Mathur, Irvine, CA (US); Andrew G. Hood, Mountain View, CA (US)

(73) Assignee: Biomet Biologics, LLC, Warsaw, IN (US)

( * ) Notice: Subject to any disclaimer, the term of this patent is extended or adjusted under 35 U.S.C. 154(b) by 203 days.

(21) Appl. No.: 14/613,403

(22) Filed: Feb. 4, 2015

(65) Prior Publication Data

US 2015/0144561 A1 May 28, 2015

Related U.S. Application Data

(62) Division of application No. 13/738,538, filed on Jan. 10, 2013, now Pat. No. 8,961,445, which is a division
(Continued)

(51) Int. Cl.
*A61M 37/00* (2006.01)
*A61M 1/36* (2006.01)
(Continued)

(52) U.S. Cl.
CPC ............... *A61M 1/36* (2013.01); *A61M 1/34* (2013.01); *A61M 1/3693* (2013.01); *A61M 1/3696* (2014.02); *A61M 1/38* (2013.01); *B01D 19/0068* (2013.01); *B01D 21/262* (2013.01); *B01D 61/145* (2013.01); *B01D 61/16* (2013.01); *B01D 61/18* (2013.01); *B01D 61/22* (2013.01); *B04B 5/0442* (2013.01); *B04B 13/00* (2013.01); *B01D 2221/10* (2013.01); *B01D 2311/04* (2013.01); *Y10T 29/49826* (2015.01)

(58) Field of Classification Search
CPC ........ A61M 1/36; A61M 1/34; A61M 1/3693; B01D 61/145; B01D 61/262; B01D 61/18; B01D 221/10; B01D 19/0068
See application file for complete search history.

(56) References Cited

U.S. PATENT DOCUMENTS

| 3,145,713 A | 8/1964 | Latham |
| 4,151,844 A | 5/1979 | Cullis et al. |

(Continued)

FOREIGN PATENT DOCUMENTS

EP    1110566 A2   6/2001

OTHER PUBLICATIONS

International Search Report regarding Application No. PCT/US03/12791.

*Primary Examiner* — Leslie Deak
(74) *Attorney, Agent, or Firm* — Schwegman Lundberg & Woessner, P.A.

(57) ABSTRACT

This invention provides an apparatus and methods to consistently separate and concentrate selected blood components. The system includes, e.g., a computerized fluid handling system to transfer blood components between a centrifugal blood separation disc, containers and a concentrator.

1 Claim, 12 Drawing Sheets

Related U.S. Application Data of application No. 12/874,467, filed on Sep. 2, 2010, now Pat. No. 8,361,005, which is a division of application No. 10/422,369, filed on Apr. 23, 2003, now Pat. No. 7,806,845.

(60) Provisional application No. 60/375,549, filed on Apr. 24, 2002.

(51) Int. Cl.

| | | |
|---|---|---|
| *A61M 1/34* | (2006.01) | |
| *A61M 1/38* | (2006.01) | |
| *B01D 19/00* | (2006.01) | |
| *B01D 61/14* | (2006.01) | |
| *B01D 61/16* | (2006.01) | |
| *B01D 61/18* | (2006.01) | |
| *B01D 61/22* | (2006.01) | |
| *B04B 5/04* | (2006.01) | |
| *B04B 13/00* | (2006.01) | |
| *B01D 21/26* | (2006.01) | |

(56) References Cited

U.S. PATENT DOCUMENTS

| | | |
|---|---|---|
| 4,342,420 A | 8/1982 | Rosemeier et al. |
| 4,498,983 A | 2/1985 | Bilstad et al. |
| 4,776,964 A | 10/1988 | Schoendorfer et al. |
| 4,911,703 A | 3/1990 | Lysaght et al. |
| 4,911,833 A | 3/1990 | Schoendorfer et al. |
| 5,030,215 A | 7/1991 | Morse et al. |
| 5,055,198 A | 10/1991 | Shettigar |
| 5,585,007 A | 12/1996 | Antanavich et al. |
| 5,607,579 A | 3/1997 | Latham, Jr. et al. |
| 5,858,746 A | 1/1999 | Hubbell et al. |
| 6,074,335 A | 6/2000 | Headley et al. |
| 6,200,287 B1 | 3/2001 | Keller et al. |
| 6,368,298 B1 | 4/2002 | Beretta et al. |
| 6,491,656 B1 | 12/2002 | Morris |
| 7,806,845 B2 | 10/2010 | Arm et al. |
| 8,361,005 B2 | 1/2013 | Arm et al. |
| 8,961,445 B2 | 2/2015 | Arm et al. |

BLOOD SEPARATION AND CONCENTRATION SYSTEM

CROSS-REFERENCE TO RELATED APPLICATIONS

This application is a divisional of U.S. application Ser. No. 13/738,538, filed Jan. 10, 2013, which is a divisional of U.S. application Ser. No. 12/874,467, filed Sep. 2, 2010 (issued Jan. 29, 2013 as U.S. Pat. No. 8,361,005), which is a divisional of U.S. application Ser. No. 10/422,369 filed Apr. 23, 2003 (issued Oct. 5, 2010 as U.S. Pat. No. 7,806, 845) which claims benefit of U.S. Provisional Application No. 60/375,549, "Blood Separation and Concentration System", by Douglas M. Arm, et al., filed Apr. 24, 2002. The full disclosures of the prior applications are incorporated herein by reference.

FIELD OF THE INVENTION

This invention is in the field of automated blood component separation and concentration systems. The present invention relates to, e.g., a system for computerized fluid handling, blood component separation and blood component concentration. The system, e.g., automatically separates blood components by density, collects particular components, concentrates selected components and reconstitutes remaining components, e.g., for possible reinfusion.

BACKGROUND OF THE INVENTION

Whole blood is made up of many components, including red blood cells, white blood cells, platelets and plasma. Although whole blood is useful, e.g., in blood replacement therapy during surgical procedures, individual blood components also have substantial utility in replacement therapies, coagulation therapy, wound healing and tissue regeneration, as described below.

Red blood cells (RBCs) are flexible biconcave cells packed with hemoglobin which carry oxygen throughout the body. RBCs are the most dense whole blood component and thus can be readily separated from whole blood, e.g., by centrifugation or even by permitting settling under the force of gravity. Packed red cells can be transfused back into a donor patient (autologous transfusion) or transfused into a patient with a compatible blood type, e.g., having an appropriate A, B, AB, O and rh antigen type.

White blood cells (WBCs) are a diverse array of cell types, e.g., lymphocytes, macrophages, and polymorphonuclear neutrophils (PMNs), which are primarily involved with immune responses and fighting infections. WBCs are generally somewhat less dense than RBCs and, together with platelets, form a white "buffy coat" layer on top of RBCs during centrifugation of whole blood. Buffy coats can be a useful source of growth factors, blast cells and cytokines.

Platelets are cell fragments shed into the blood stream by large megakaryocyte cells in the bone marrow. Platelets play an important role in coagulation of blood. When platelets contact damaged blood vessels, they aggregate and send chemical messages that can initiate the coagulation cascade. Patients with reduced peripheral blood platelet counts, e.g., patents with certain leukemias or sickle cell anemia, may require transfusions of platelets to help control bleeding episodes. Platelets settle through plasma more slowly than RBCs and WBCs due to their low density and small size. When whole blood is centrifuged, platelets can be found distributed in the plasma, in the buffy coat, and/or in the upper portion of the red cells, depending on the centrifugation time and centripetal forces involved.

Plasma is a complex aqueous solution of proteins, lipids, small molecules and salts which acts as the transport medium for the other blood components. Plasma also contains elements necessary to the function of various biological systems, e.g., the coagulation cascade, the compliment cascade, hormones, buffers, nutrients, etc. Plasma can be stabilized with anticoagulants, e.g., citrate or heparin, for handling or storage. Plasma is the least dense of the blood components described here and presents as supernatant after centrifugation of whole blood.

Plasma and/or platelets, in the absence of active anticoagulants, or in the presence of a catalyst, e.g. thrombin, can initiate coagulation or clotting to form a wound sealant or platelet gel useful to repair damaged tissues and to stop bleeding. Such wound sealants are generally more effective when they are concentrated and contain abundant platelets. Fibrin based wound sealants produced from pooled blood components have been available in Europe. Licensing of such products for use in the United States has been prolonged due to fear of disease transmission, though the first plasma-based fibrin sealant from pooled allogeneic sources was recently cleared. However, wound sealant preparations made from a patient's own (autologous) blood present minimal risk of disease transmission.

Plasma can be harvested by filtration of blood directly from a patient. For example, in U.S. Pat. No. 4,498,983 to Bilsted, "Pressure Cuff Draw Mode Enhancement System and Method for a Single Needle Blood Fractionation System", whole blood is drawn through a needle into an apparatus wherein the blood is treated with an anticoagulant and passed over a filter to remove some plasma. The plasma depleted blood is then reinfused into the patient along with some saline to make up the blood volume. Such filtered plasma will form a clot when exposed to thrombin. However, the concentration of fibrinogen in filtered plasma is too low to act as an effective wound sealant.

A plasma preparation can also be produced by centrifugation of whole blood (see, e.g., U.S. Pat. No. 3,145,713, "Method and Apparatus for Processing Blood" and U.S. Pat. No. 4,151,844, "Method and Apparatus for Separating Whole Blood into Its Components and for Automatically Collecting One Component"). Some platelets may remain in centrifuged plasma of these inventions to add some structure when it is clotted. However, without concentration, such plasma does not have the properties of an adequate fibrin glue.

A fibrin glue wound sealant can be prepared by cryoprecipitation and centrifugation of plasma to concentrate fibrinogen. For example, a fibrin glue can be prepared by holding anticoagulated plasma in the cold to precipitate coagulation proteins, e.g., fibrinogen, followed by centrifugation to pellet and concentrate the cryoprecipitate. Just before application to a wound, thrombin is added to the cryoprecipitate to begin conversion of fibrinogen to fibrin whereby the fibrin glue clot is formed. The fibrin glue can stabilize surgical incisions and seal leaky blood vessels. Although such procedures can be helpful, they suffer from the time and effort required, the waste of disposed blood components, and the bulky equipment involved. Cryoprecipitated fibrin glues, particularly from autologous plasma, are not a practical solution to wound sealing on an emergency basis.

In U.S. Pat. No. 5,585,007 to Antanavich, "Plasma Concentrate and Tissue Sealant Methods and Apparatuses for Making Concentrated Plasma and/or Tissue Sealant", whole blood is separated by centripetal force and the plasma is concentrated by selective absorption of water. This device is an improvement over prior technology in that it both separates and concentrates plasma. Fifty (50) ml of whole blood is introduced into the top centrifugal chamber of the device, then the chamber is spun to sediment blood cells about the periphery of the chamber where they are captured, e.g., by a mat matrix. The rotation of the chamber is stopped, allowing liquid components of the blood to fall into a lower chamber where they are exposed to dehydrating beads which concentrate the liquid components to some extent.

The Antanavich device lacks the flexibility required to accommodate different amounts of whole blood starting material, to adjust for variations in blood component proportions, or to control the character of concentrated products. For example, depending on the hematocrit of the whole blood, various amounts of liquid components remain trapped in the upper chamber and various proportions of water are removed by the dehydrating beads. Fine tuning the device to harvest special component mixtures, e.g., buffy coat, is not possible. In addition, many blood components, e.g. white blood cells, can not be collected or reinfused as they are lost in the device as waste material.

There remains a need to provide an automated system to quickly and consistently separate and concentrate selected blood components in a single aseptically sealed instrument. Waste of blood components needs to be reduced by provision of technologies for high recovery and reconstitution of unselected blood components for reinfusion.

SUMMARY OF THE INVENTION

The present invention provides an automated apparatus to consistently separate and/or concentrate blood components. The apparatus can include a separation disc, a concentrator and a control system to monitor and direct the flow of, e.g., blood and blood components, between containers. The apparatus can include a disposable component kit that is sterile, aseptically sealed and easily to load into the apparatus.

In one aspect, the apparatus includes a whole blood container, a separation disc, a pump, a concentrator, a valve, a control system and detectors. Whole blood in the container can include blood components with differing densities and molecules with various molecular weights. Blood, as used herein, can include, various suspensions of cells including, e.g., whole blood, other animal blood products, eukaryotic or prokaryotic cell culture fluids, and the like. The separation disc, mounted to rotate in the apparatus, has a first port in fluid communication with the whole blood container through a first conduit, and has a second port, e.g., near the disc axis of rotation. The pump can drive whole blood and blood components from the container through the first conduit to the separation disc and out the second port to the concentrator. The concentrator can have, e.g., an ultrafiltration membrane with a retentate side and permeate side and is in fluid communication with the second port of the separation disc through a second conduit. The valve can control, e.g., transfer of blood components through the second conduit. The control system can control, e.g., the pump, and the valve, to direct transfer of the blood between the container, the separation disc, and/or the concentrator. The detector can be connected to the control system and mounted on the apparatus in operative orientation to detect the fill level of the separation disc. In operation, for example:

1) the control system directs the transfer of blood from the container to the separation disc, 2) the separation disc rotates, creating a centripetal force which separates blood components in order of density, 3) high density components accumulate at the periphery of the separation disc, and low density components, and/or intermediate density components, accumulate near the second port, 4) the high density components accumulate to a level that triggers the detector which transmits a signal to the control system, and, 5) the control system directs the valve to open allowing low density components and/or intermediate density components to flow from the separation disc outlet port into the concentrator and onto the retentate side of the membrane where the low molecular weight molecules pass through to the permeate side of the membrane, whereby the low density components and/or intermediate density components are concentrated into concentrated blood components.

In a more basic form, the apparatus to produce concentrated blood components can comprises, e.g., a separation disc, a control system and a concentrator. The separation disc can receive blood through a first conduit and rotate, generating centripetal force, to separate the blood components according to density. The control system can direct operation of a first pump operably coupled to the first conduit to transfer blood and/or blood components to the separation disc. The separated blood components can include, e.g., plasma or buffy coat. The concentrator can receive separated blood components from the separation disc, through a second conduit, onto the retentate side of an ultrafiltration membrane. During operation of the apparatus, low molecular weight molecules in the blood components can be forced, by pressure, through the membrane to the permeate side of the membrane leaving the blood components concentrated on the retentate side. The concentrated blood components are a composition of the invention. The apparatus can automatically process, e.g., 100 to 500 ml of blood from a first container through the conduit and separation disc.

The apparatus of the invention can have the separation disc, the centrifuge chamber, the concentrator, and the control system all within a bench top housing. The centrifuge chamber can be positioned within the apparatus on vibration isolation mounts. The separation disc can be rotatably mounted in the centrifuge chamber and locked into place with an iris-like chamber door. The iris door can be configured to center the separation disc, to comprise a port orienting keyway, to provide a mounting position for an RBC interface detector and/or to provide a force maintaining seal pressure on a rotary seal.

An RBC interface detector can be connected to the control system and mounted in operative orientation to the chamber in association with the separation disc to detect an RBC interface, buffy coat interface, or other interfaces. The control system can be connected to a junction valve which can direct separated components from the second conduit alternately to the concentrator or to a plasma container. The control system and RBC interface detector can be configured, e.g., to transfer low density components from the separation disc into the plasma container until the RBC interface is detected. The junction valve can then be switched to send selected blood components to a concentrator for concentration.

The control system can be in operatively connected (i.e., controlling power and/or receiving rotation rate information) with a drive motor that rotates the separation disc, and operatively connected (i.e., controlling actuation) to a valve operably coupled to the second conduit to direct the flow of separated components in the second conduit. The control system can set the separation speed to produce a force of about 2000×g during blood component separations. The control system can slow the rotation of the separation disc to produce a force between about 500×g and about 1000×g after detection of the RBC interface and direct opening of the valve to collect certain blood components. The composition of the blood components can be affected, e.g., by mounting the RBC level detector to trigger at a predetermined level of blood components in the separation disc. The control system can optionally pause separation and/or concentration operations to allow sampling of blood components before completion of processing. The control system can be operably connected to an air detector operatively coupled to the first conduit so that the pump will be stopped when air is detected in the first conduit.

The control system can be connected to an RBC detector on the second conduit to stop the first pump when RBCs are detected coming out of the separation disc. This mechanism can provide sharp resolution in the harvest of closely associated blood components, e.g., separated RBCs, WBCs and platelets. In addition, this mechanism can establish the end of a separation process pass and signal time to initiate transfer of depleted RBCs to a holding container. The control system can be connected to a junction valve operably coupled to the first conduit to direct transfer of residual blood components from the separation disc to an RBC holding container when the first pump is operated in reverse. Blood components, which were not sent to the concentrator, can be reconstituted by transferring separated components, to the RBC holding container, thereby reconstituting the residual blood component from the separation disc with separated components that were not received by the concentrator. Reconstituted components can be suitable for infusion into a patient or they can be further processed by the apparatus of the invention.

Concentrated blood components prepared by the apparatus of the invention are another aspect of the invention. The concentrated blood components can include growth factors present at levels 2-fold or more over peripheral blood levels. Concentrated growth factors of the invention can include, e.g., IGF, EGF at a concentration of about 100 pg/ml or more, FGF at a concentration of about 150 pg/ml or more, VEGF at a concentration of about 800 pg/ml or more, PDGF at a concentration of about 30 ng/ml or more, and/or TGF at a concentration of about 200 ng/ml or more.

The control system of the invention can be operably connected to detectors, e.g., pump turn counters, air detectors, optical array volume detectors and RBC detectors, to detect collection end points and to provide for calculation of component volumes. For example, the first pump can have a turn counter connected to the control system which can determine transferred blood volumes ($V_b$) from the start of processing to the time air is detected in the first conduit. In another example, the volume of filtrate ($V_f$) through the permeate side of the membrane can be detected by an optical array volume detector mounted to the holding container and connected to the control system.

The control system can receive an expected blood volume ($V_{eb}$) from an operator interface and compare it to the determined blood volume ($V_b$), then issue a notice to the operator if the expected and determined blood volumes do not match within about 30%, or more. The control system can calculate an expected separated blood component volume ($V_{sce}$) by multiplying a separation factor, e.g., in the range of about 0.25 to about 0.4, times the lesser of the determined blood volume ($V_b$) and the expected blood volume ($V_{eb}$). A table or spreadsheet can be provided with an array of such calculations for ready reference by an operator. The control system can terminate separation processes by stopping the first pump when the volume of the separated components ($V_{sc}$) equals the expected separated component volume ($V_{esc}$). The control system can also terminate the concentration process when the volume of concentrated separated components ($V_{csc}$) equals the volume of the separated components ($V_{sc}$) multiplied by a concentration factor, e.g., about 0.2 to about 0.4.

A disposable kit of the invention can include, e.g., the first conduit, the separation disc, the second conduit and/or the concentrator, which can all be loaded into the top of the apparatus. The first conduit and the second conduit can comprise peristaltic tubing. The disposable kit can be fabricated with one or more cassettes that guidedly mount, e.g., the conduit into valves, the conduit into detectors, and/or the conduit into pumps. Such cassettes can, e.g., firmly "snap" conduit into functional association with valves, pumps and detectors in a fashion appreciated by those skilled in the art. The disposable kit components can be plastic and packaged in a sealed container, such as a plastic pouch or tray, and sterilized with gamma radiation.

The separation disc can include a rotary seal, an inlet port, an outlet port, a keyway, a bowl, welded ribs and radial channels. The rotary seal can include a rubber seal spring which can be press-fitted into a graphite seal. The bowl can have an aspect ratio of 1 to 5, or less, to improve resolution of separated components. The inlet port and outlet port can be oriented in the same direction and a keyway can direct the pair of ports as the separation disc is loaded into the apparatus.

The concentrator of the invention can be a tangential flow filter, e.g., a hollow fiber filter. The concentrator can have an ultrafiltration membrane with a molecular weight cut off of 2-150 kDa. A pressure gradient across the membrane can be provided by a fluid pump on the retentate side of the membrane or from a vacuum pump on the permeate side of the membrane. The concentrator can be part of a recirculating loop including the second conduit, a second pump operatively coupled to the conduit, and a second container. The control system can be connected to the pump to direct recirculation of separated components in the concentration loop.

The present invention provides a method of producing concentrated blood components by processing blood with the apparatus of the invention. In one embodiment of the method, e.g., RBCs are detected in a separation disc at detection levels predetermined to provide a desired composition of separated blood components; separated components are collected from an outlet port proximate to the separation disc rotational axis until RBCs are detected in the collection stream; separated components are transferred to a concentrator; and, separated components are concentrated by ultrafiltration. Blood or blood components can be continuously loaded onto the separation disc while it is spinning. Separated components can be harvested in repeated milking cycles of collecting not more than about 10% of a separation disc volume and pausing collection for a time period before collecting again. In some embodiments, a pause in the cycle can allow the interface to stabilize between collections for improved resolution of blood components. The method of the invention can provide for the detection, collection, transfer, and concentration steps all in a single bench top instrument. The method provides a control system for monitoring detection, directing collection, directing transfer, and/or directing concentration.

The method of the invention additionally provides the steps of determining a total blood volume ($V_b$) loaded onto the separation disc, monitoring a separated component volume ($V_{sc}$), calculating an expected separated component volume ($V_{sce}$), and ending collection of separated components when the separated component volume ($V_{sc}$) equals the expected separated component volume ($V_{sce}$). The expected separated component volume ($V_{sce}$) can be calculated by multiplying the total blood volume ($V_b$) by a separation factor. Collection of separated components volume ($V_{sc}$) can be ended when an expected concentrated component volume ($V_{cce}$) equals a monitored concentrated component volume ($V_{cc}$). The expected concentrated component volume ($V_{cce}$) can be calculated as the separated component volume ($V_{sc}$) multiplied by a concentration factor. The concentrated component volume ($V_{cc}$) can be calculated as the separated component volume ($V_{sc}$) minus a concentrator filtrate volume ($V_f$).

Another aspect of the methods of the invention is manufacturing a disposable set by fabricating a separation disc coupled through a conduit to a concentrator. The manufacture of the disposable set can additionally include fabricating one or more cassettes configured to guidedly mount the disposable set to an apparatus. The method of the invention can further include the step of loading the disposable set into the apparatus.

The present invention includes separated and concentrated blood components produced by the methods of the invention. Platelet poor plasma can be collected from the outlet port before the RBC interface is detected. Prothrombin in the platelet poor plasma can be converted into thrombin for use, e.g., in preparation of coagulated products of the invention. Concentrated blood components can be contacted with thrombin to prepare a fibrin gel, a wound sealant, and/or a bone graft substitute. The method can include isolating one or more growth factors, compliment cascade proteins and/or coagulation factors from the concentrated blood components.

DEFINITIONS

Before describing the present invention in detail, it is to be understood that this invention is not limited to particular compositions, methods, or systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a container" can include a combination of two or more containers; reference to "media" can include mixtures of media, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

The term operably connected, as used in association with the control systems of the invention, refers to functional connections between the control system and apparatus components. Such connections can include, e.g., communication lines between the control system and detectors or actuators, computer interface or relay control of power supply cables to valves or motors, and the like.

The term plasma, as used herein, refers to the non-cellular component of uncoagulated blood. Platelet rich plasma (PRP) refers to plasma which is has a concentration of platelets at least as great as whole blood. Platelet poor plasma (PPP) refers to plasma which is has a concentration of platelets less than whole blood.

The term separated blood components refers to, e.g., plasma, platelets, WBCs, RBCs and combinations thereof which comprise less than whole blood. Such combinations can include, e.g., packed RBCs, buffy coat depleted reconstituted blood, plasma-buffy coat, platelet rich plasma, and the like. In some embodiments of the invention, "blood components" can refer to components of cell suspensions other than blood, such as bacterial cell cultures, bacterial cell suspensions, yeast cell suspensions, animal cell culture fluids, plant cell culture fluids, and the like. That is, although the preferred use of methods, apparatus and sets of the invention are in separation and concentration of blood components, the invention can be used to separate and/or concentrate other process materials or cell suspensions.

DETAILED DESCRIPTION

The present invention provides a compact automated system to, e.g., separate blood into components, collect selected components, and to concentrate components. The invention is intended to provide concentrated blood components, e.g., concentrated buffy coat for use in purification of growth factors, autologous platelet gel, wound healants/sealants or bone growth matrixes. Components of the apparatus can be provided in a sterile, aseptically sealed, disposable kit. The invention consistently provides desired blood components without waste.

The Apparatus

The apparatus of the invention can, e.g., load the blood onto a rotating separation disc, collect lower density blood components, concentrate the blood components, remove higher density components from the disc to a holding container and repeat the process. The apparatus can include a control system with associated software, detectors and actuators to flexibly process a variety of cell suspensions into separated components and/or concentrates. The following example is offered to illustrate, but not to limit the claimed invention.

Figure 1:
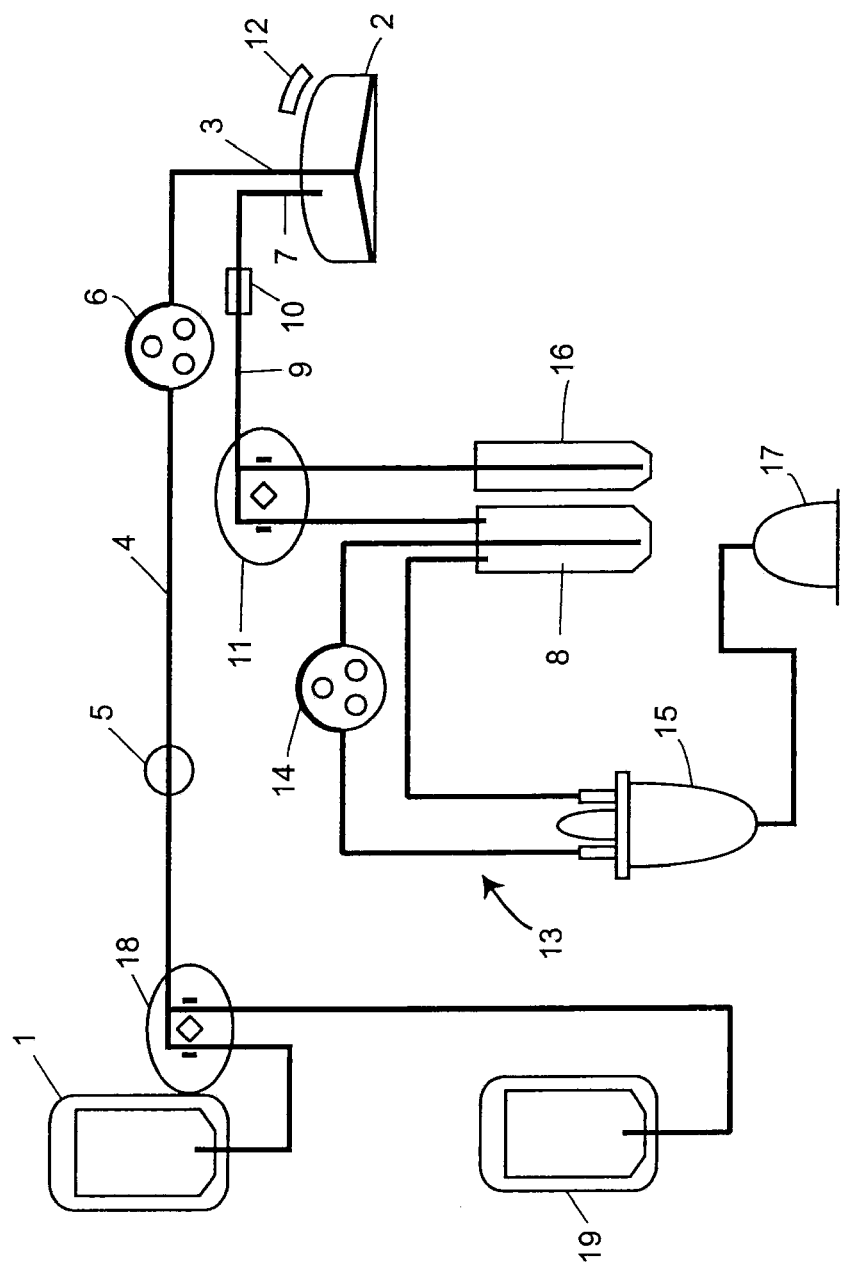
FIG. 1 is a schematic diagram of exemplary separation/concentration apparatus hardware.

As shown in FIG. 1, the hardware for the apparatus can, e.g., include whole blood (first) container 1 in fluid connection with separation disc 2 at inlet port 3, through first conduit 4 associated with air detector 5 and first pump 6. Outlet port 7 of separation disc 2 is in fluid connection with concentrate holding (second) container 8 through second conduit 9 associated with RBC detector 10 and (second) valve 11. RBC level detector 12 is associated with separation disc 2 to detect an RBC interface in the working apparatus. Recirculating concentrator loop 13 includes concentrate holding container 8 in fluid connection with (second) pump 14 and concentrator 15.

In one mode of operation, whole blood load container 1 holds blood to be separated and/or concentrated. The blood is transferred through first conduit 4, by the driving force of first pump 6, to fill rotating separation disc 2. The blood is separated into components by centripetal force. Lower density components, e.g., plasma, are pushed out outlet port 7, located proximate to an axis of rotation of separation disc 2, and into plasma holding container 16. As blood cells accumulate in at the periphery of separation disc 2, the RBC interface eventually rises to trip RBC level detector 12 causing valve 11 to switch for buffy coat collection in concentrate holding container 8.

Simultaneous with (or independent of) the separation process above, second pump 14 can circulate buffy coat from concentrate holding container 8 through concentrator 15 and back to concentrate holding container 8. As buffy coat recirculates through concentrator 15, a pressure gradient is provided by vacuum pump 17 in fluid communication through a conduit to a permeate side of a concentrator membrane to force low molecular weight molecules through the membrane as a filtrate.

Buffy coat can be collected until RBCs begin to exit separation disc 2 and are detected by RBC detector 10. First pump 6 is then operated in reverse to empty separation disc 2. First (junction) valve 18 is switched to divert flow from first conduit 4 into RBC holding container 19. Second valve 11 can switch to allow first pump 6 to transfer plasma from plasma holding container 16 into RBC holding container 19 to reconstitute plasma and RBCs as buffy coat depleted blood.

A hematocrit for the whole blood loaded onto the apparatus can be calculated, e.g., based on an algorithm and process parameters. For example, the volume of blood that has been loaded by the time RBCs are detected at the RBC detector be related to the hematocrit of the blood. Algorithms, equations, or tables can be developed, based on theory or empirical data, to estimate the hematocrit bases on load volume before RBC detection. Estimated hematocrit values can be input to other algorithms, equations, or tables to calculate other process parameters, such as, e.g., expected buffy coat volume, expected plasma volume, expected RBC volume, and/or the like. Such process parameters can be used, e.g., by the control system to adjust other processing parameters, such as, e.g., flow rates, separation disc rotation rates, plasma concentration end points, and/or the like.

After the first pass of the separation cycle described above, the apparatus can initiate additional passes until the whole blood load is emptied from whole blood container 1. As the last of the blood is transferred from whole blood container 1, air enters and triggers air detector 5. At this point, first valve 18 can switch to allow processing to continue using depleted blood from RBC holding container 19. Separation of components from blood and/or depleted blood can continue until a desired volume of components has been obtained.

Concentration of separated blood components can continue while additional separated blood components are added to the recirculating concentration loop with every pass of the separation cycle. Concentration is complete when the volume of concentrated separated components is a desired fraction of the total collected separated components.

Although the above description refers primarily to separation and concentration of buffy coat, other blood components can also be prepared with the apparatus. For example, if valve 11 is open from the start of processing so that all separated plasma flows to concentrate holding container 8, and if RBC level detector 12 is set to trip just before buffy coat exits separation disc 2, the final product can be a platelet rich plasma concentrate. Similarly, if separation disc 2 is loaded, e.g., more slowly and/or rotated faster to remove more platelets from plasma, and if the plasma is directed to concentrate holding container 8 without buffy coat, a platelet poor plasma concentrate can be prepared.

In addition to the components described above, the apparatus can include a control system, e.g., with detectors, actuators, an operator interface and programmed software, to automate the processing of blood and blood components.

Modifications to, e.g., pump flow rates, separation disc speeds, concentration levels, valve timing, detector sensitivity and detector locations, will be apparent to those in the art, without undue experimentation, for provision of a variety of blood components. The apparatus of the invention can be configured to provide, e.g., packed red cells, buffy coat depleted blood, buffy coat, platelet rich plasma, platelet poor plasma, concentrated buffy coat, concentrated platelet rich plasma, concentrated platelet poor plasma, plasma filtrates, and/or the like. It can be appreciated by those in the art that the apparatus of the invention can separate and/or concentrate components of a variety of cell suspensions, such as cord blood, disaggregated bone marrow tissue, cultured cell suspensions, homogenized glandular organs, and the like.

The Separation Disc

The blood component centrifuge of the invention is, e.g., a low volume, high resolution separation disc capable of continuous loading while in operation. The separation disc can work, e.g., in conjunction with computer coupled pumps, valves and detectors, to consistently provide desired blood component concentrates.

Whole blood contains a variety of components that vary in size and density. These differences can be taken advantage of to separate the components. For example, red blood cells (RBCs) are more dense than certain other blood components, e.g., white blood cells (WBCs), platelets and plasma. RBCs readily settle out of anticoagulated whole blood under the force f gravity or in a centrifuge. WBCs are generally larger than RBCs but are less dense and settle later in a layer called a buffy coat. Platelets are relatively low density cell fragments that settle last leaving clarified plasma. Finally, under high centripetal force, colloidal chylomicrons can migrate to the surface of plasma as a low density fatty layer.

The apparatus of the invention can be configured with the separation disc to automatically isolate, e.g., platelet poor plasma, platelet rich plasma, buffy coat, packed RBCs, and/or other desired separated or concentrated blood components.

The separation disc of the invention can be, e.g., a low volume transparent disc with a low aspect ratio (height to diameter). The disc has, e.g., an inlet port feeding fluid to the periphery of the disc through a series of radial channels, and an outlet port proximate to the disc axis of rotation. The ports can gain access to the disc through a rotary seal.

The separation disc can have a low volume, e.g., 45 ml or less, thus allowing a low over all system volume. The low separation disc volume in combination with the ability to make multiple passes of the separation cycle adds to the flexibility of the system. For example, should the operator require only 10 ml of concentrated plasma, the system may require only, e.g., 100 ml of whole blood. The concentrated plasma product can be provided in one pass of the separation cycle. Alternately, a large amount of concentrated plasma-buffy coat might be needed to prepare bone growth matrix for bone repair. Where large amounts of concentrated components are required, the apparatus can be loaded with, e.g., 500 ml or more of whole blood. The 500 ml can be processed in, e.g., 5 or more passes through the separation cycle noted above. The ability to receive a small volume load and/or to perform repeated separation cycles provides the apparatus flexibility in processing a wide range of load material starting volumes.

The separation disc of the invention can have a low aspect ratio. That is, the internal sample chamber (bowl) can have a height significantly less than the diameter of the disc. A benefit of a low aspect ratio sample chamber can be faster and better resolution of blood components. For a given volume, a low aspect ratio provides a greater proportion of sample at the periphery where the separating g-forces are highest. Such a design is particularly beneficial in a low volume system.

The separation disc has, e.g., inlet and outlet ports in fluid contact with the separation disc internal chamber through a rotary seal. The rotary seal is intended to allow the separation disc to spin while it continuously receives additional load material (continuous processing). The rotary seal is also intended to provide a seal to gas and liquid as an element of an overall sealed system to prevent operator contact with blood samples and to prevent cross contamination between sequentially processed samples.

Figure 2:
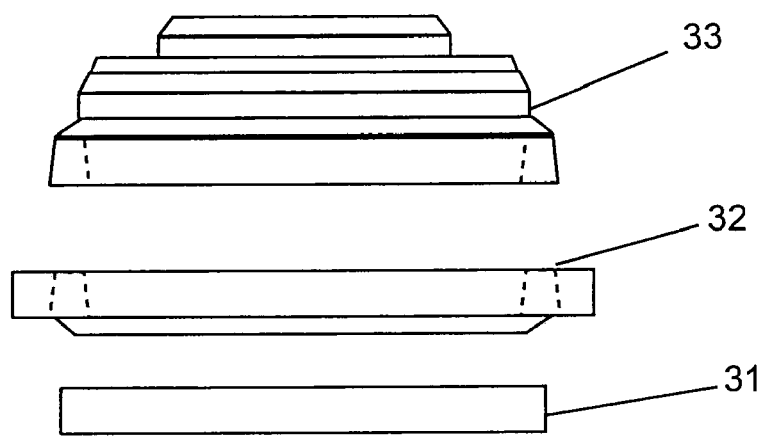
FIG. 2 is a schematic of a rotary seal blow-up diagram.

The rotary seal (see, FIG. 2) can be fabricated, e.g., from three elements: ceramic seal 31, graphite seal 32, and rubber seal spring 33. In a working embodiment of the design, the inlet port and the outlet port are sealed by, and pass through, rubber seal spring 33. Rubber seal spring 33 is press-fitted into graphite seal 32 without need for additional components, such as a ring-clip or compression spring, to hold it in place. Graphite seal 32 has a rubbing surface in sealed contact with ceramic seal 31 at the top of the separation disc (not shown). Rubber seal spring 33 not only provides a hermetic seal to the ports and at graphite seal 32, but can also provide a spring pressure to graphite seal 32 maintaining the sealed rubbing contact between graphite seal 32 and ceramic seal 31.

The inlet port of the separation disc can enter at the axis through the rotary seal and feed sample to the periphery of the separation disc internal chamber through a series of radial channels. For a low volume system, this design is an improvement over previous centrifuge bowl designs which feed fluid to fan out in a thin chamber behind the bowl floor. The radial channels have a much lower volume than the thin chamber designs and thus transport fluid faster to the working periphery of the separation disc. Fluids in the radial channels have less time to separate into components before entering the main internal chamber, thus, e.g., reducing clogging. Radial channels of the invention aid separation and recovery, e.g., by quickly transporting a homogenous mixture of components to the working separation chamber.

The outlet port can be located proximate to the separation disc axis of rotation to receive, e.g., lower density blood components separated in the disc. In continuous feed operation, components exiting at the outlet port can become increasingly dense as additional load material is loaded at the periphery of the separation disc through the fluid channels. The capability of the invention to discretely select the components for collection as they exit the outlet port enhances the resolution and recovery of the apparatus of the invention.

In one embodiment, the outlet port is oriented in the same direction as the inlet port. This orientation has the advantage of minimizing tubing lengths and thus a system dead volume. This orientation can also direct the associated tubing (conduit) to prevent entanglement and to aid in loading of the disposable kit (described below).

Radial ribs can be provided in association with essentially flat chamber wall (shell) sections to enhance the rigidity of the separation disc. The ribs can prevent flexion of the chamber walls and resultant changes to the chamber volume that can disturb separated components. The ribs can be applied in any conventional fashion such as, e.g., gluing, injection molding or welding.

The separation disc can be mounted to a drive motor through a mounting chuck. In one embodiment, a centrifugal chuck comprises a plurality of axially pivoting fingers operably weighted such that rotation of the chuck urges the fingers to grip the separation disc more tightly.

The separation disc can be fabricated from any materials known in the art. In one aspect of the invention, the separation disc is disposable. In another aspect, the separation disc is sterilized with gamma irradiation. In still another aspect of the invention, a blood component, e.g., RBC, interface is detected through transparent walls of the separation disc by a detector mounted in operative orientation outside in association with the separation disc. Typically, the separation disc is made from a rugged transparent plastic, e.g., polycarbonate, stable to gamma irradiation.

The separation disc of the invention can be mounted in a centrifuge chamber to provide containment and structural support.

Figure 3:
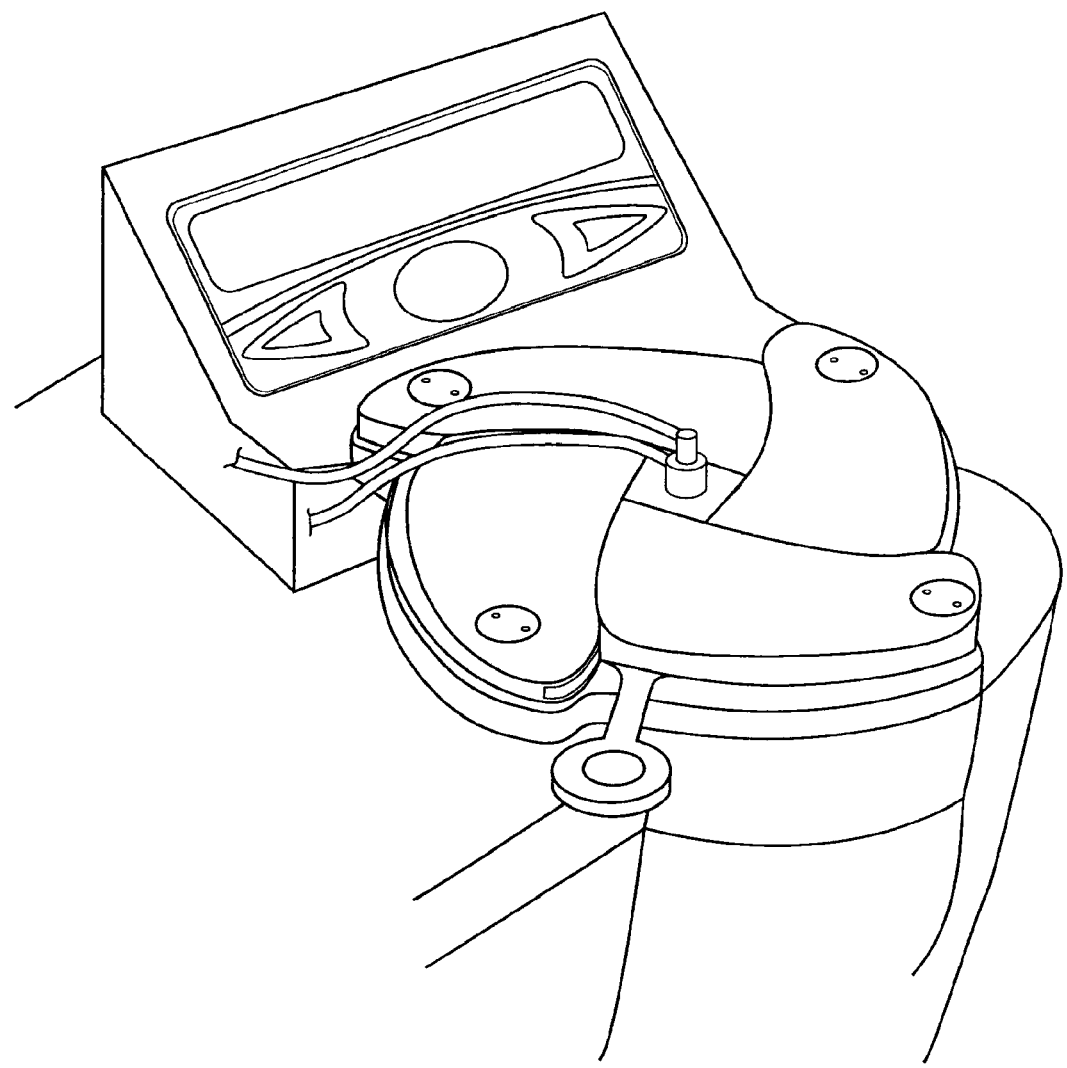
FIG. 3 is a schematic diagram of a closed centrifuge chamber iris door centering and directing the separation disc ports.

One embodiment of the invention provides an iris door (see FIG. 3) to the centrifuge chamber. The iris configuration can provide centering of the separation disc. The leaves of the iris door can close in toward the center of the chamber opening to, e.g., centrally contact and centrally mount the top of the separation disc, including the inlet and outlet ports. As the iris door locks closed, the separation disc can be urged into a position, e.g., precisely centered and aligned with a drive motor and drive chuck for balanced rotation. A keyway can be included in the iris door, e.g., to receive a projection from the separation disc, whereby the inlet and outlet ports can be properly oriented for loading of a disposable kit. The iris door can provide a mounting surface for one or more RBC level detectors.

The separation disc can be seated into position by the iris door. For example, projections from the iris leaves can be received into an annular groove in the separation disc. The projections can have an inclined surface which contacts the lower surface of the annular groove to force the groove and disc down as the leaves close. The downward force can compress the rubber seal spring to provide a force for maintainance of sealing pressure between the graphite seal and the ceramic seal.

The Concentrator

The concentrator of the invention can be, e.g., a capsule housing an ultrafiltration membrane to receive separated blood components for tangential flow concentration. The concentrator can be part of a recirculating loop, including a conduit, a pump and a holding container. The concentrator can concentrate or filter separated components in the recirculating concentration loop simultaneous with an ongoing separation operation.

Ultrafiltration membranes are, e.g., sheets or tubes of material having microscopic pores that allow some small (low molecular weight) molecules to pass through the membrane while retaining larger (high molecular weight) molecules. The membranes of the concentrator can be, e.g., regenerated cellulose, polysulfone, or polyethersulfone membranes with a molecular weight cut-off of, e.g., from about 2 kDa to about 150 kDa. Tangential flow membranes are one aspect of the invention in which a separated component is pumped tangentially across the membrane surface. Tangential flow scours the membrane surface and is particularly useful in preventing suspended particulates from clogging membrane pores. Hollow fiber membranes are a type of tangential flow membrane that can have a high ratio of membrane surface to sample volume, providing rapid transfer of low molecular weight molecules across the membrane.

In practice, separated components can be applied to the retentate side of the membrane. A pressure gradient can be applied across the membrane wherein the pressure on the retentate side of the membrane is greater than the pressure on the permeate (filtrate) side of the membrane. The pressure difference tends to force the low molecular weight molecules through the membrane while cells and high molecular weight molecules, which do not fit through the membrane pores, are retained. The pressure gradient can be provided by pumping fluid onto the retentate side of the membrane. In one embodiment, the pressure gradient results from application of a lower pressure (vacuum) to the permeate side of the membrane. In this embodiment, the pressure gradient is automatically limited to, e.g., about 1 bar, thereby minimizing the possibility of overpressure membrane damage or membrane clogging from overly rapid filtration.

The concentrators of the invention can be beneficially fabricated from disposable materials amenable to sterilization with gamma irradiation. For example, the concentrator housing can be fabricated from polycarbonate and the membranes from regenerated cellulose.

In one aspect of the invention, the concentrators are part of a recirculating loop. Separated components can be pumped from a concentrate holding (second) container, across the concentrator and back to the container. A recirculating system is particularly appropriate to a tangential flow system where less concentrated components can scour and flush more concentrated components back to the container, preventing membrane fouling.

The invention provides, e.g., a concentrator housed in a U-shaped capsule having the sample inlet and the retentate outlet juxtapositioned. This capsule shape can minimize tubing length and system dead volume. This capsule shape can also aid in easy loading of the disposable kit, as described below.

The Control System

The control system of the apparatus can, e.g., receive input data, store data, make calculations, and direct operations to carry out an automated blood separation and concentration process. For example, the control system can command a pump to load the separation disc, calculate the load volume, detect when buffy coat can be harvested, direct the buffy coat to the concentrator, and determine when the buffy coat is concentrated to the extent desired by an operator or as specified in a programmed instruction set.

The control system can include, e.g., a separate desk top computer system, or one or more computers can be integrated into the housing of the apparatus. Computers, here, can refer to, e.g., CPUs, integrated circuits, digital control modules, portable computers, lap tops, desk tops, servers, main frames, and/or the like. A controller can be capable of, e.g., carrying out all the input, data storage, calculation, and/or command operations of the invention. Alternately, the operations can be divided among several controllers. The term control system, as used herein, refers to a computer, a controller or more than one controller, operably connected to other components of the apparatus of the invention.

Systems in the present invention can include, e.g., a digital computer with data sets and instruction sets entered into a software system to practice the methods described herein. The computer can be, e.g., a PC (Intel x86 or Pentium chip-compatible with DOS®, OS2® WINDOWS®, WINDOWS NT®, WINDOWS95®, WINDOWS98®, or WINDOWSXP® operating systems) a MACINTOSH®, Power PC, or SUN® work station (compatible with a LINUX or UNIX operating system) or other commercially available computer which is known to one of skill. Software for process control is available, or can easily be constructed by one of skill using a standard programming language such as Visualbasic, Fortran, Basic, Java, or the like.

Typically, the control system of the invention includes a flat panel display, a microprocessor, memory, interface circuits and touch pad integrated into the housing of the apparatus. However, any control system of the invention optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Input devices, such as a keyboard or mouse, optionally provide for input from a user, e.g., selection of options or actions for the control system to act upon.

The control system can include appropriate software for requesting and/or receiving user instructions, either in the form of user input into a set parameter fields, e.g., in a GM, or in the form of preprogrammed instruction sets. The software can then, e.g., convert these instructions to appropriate language for instructing the operation of the apparatus to carry out the desired operation.

In one aspect, the apparatus is a stand alone table top instrument. Such a compact design typically employs an integrated central processing unit (CPU) on a motherboard to handle the control system computational functions. In this aspect, the CPU is not normally programmable by the user but is flexibly operated by commands from an operator interface (discussed below).

Figure 4:
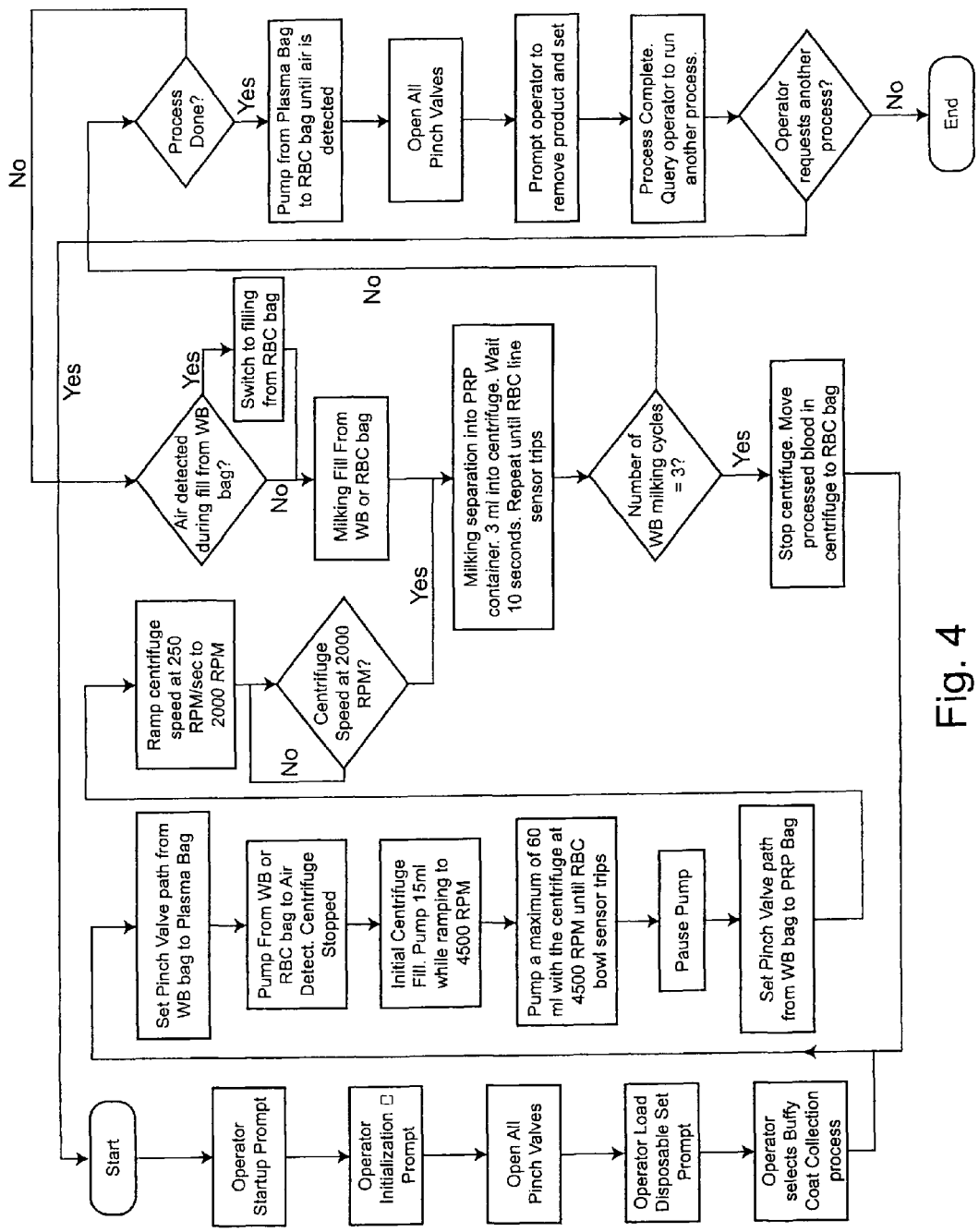
FIG. 4 is a schematic block flow diagram of an exemplary apparatus operation software design.
Figure 5:
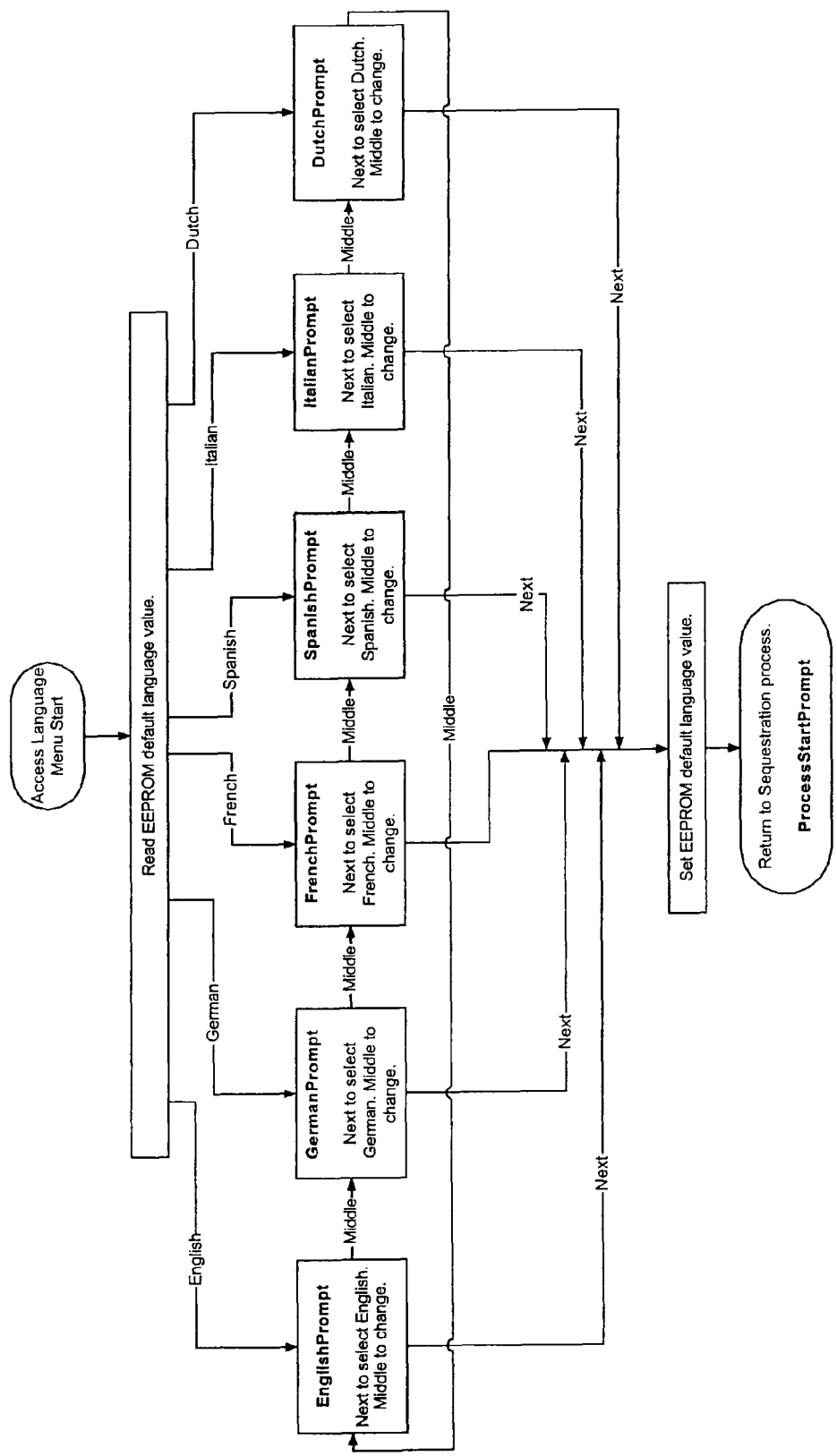
FIG. 5 is a schematic block flow diagram of an exemplary software design for a apparatus operator interface language selection.
Figure 6:
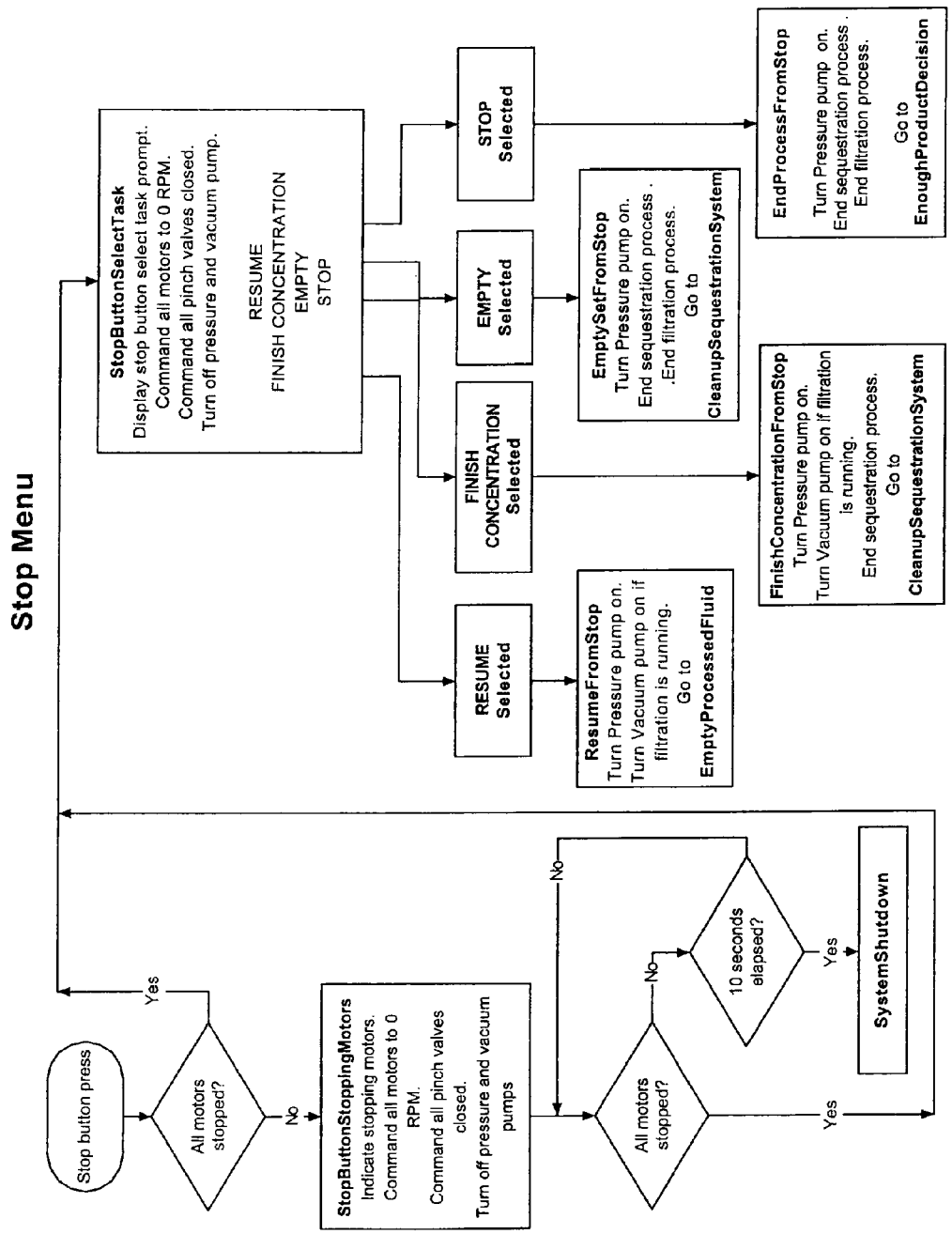
FIG. 6 is a schematic block flow diagram of an exemplary software design for manual stop responses.
Figure 7:
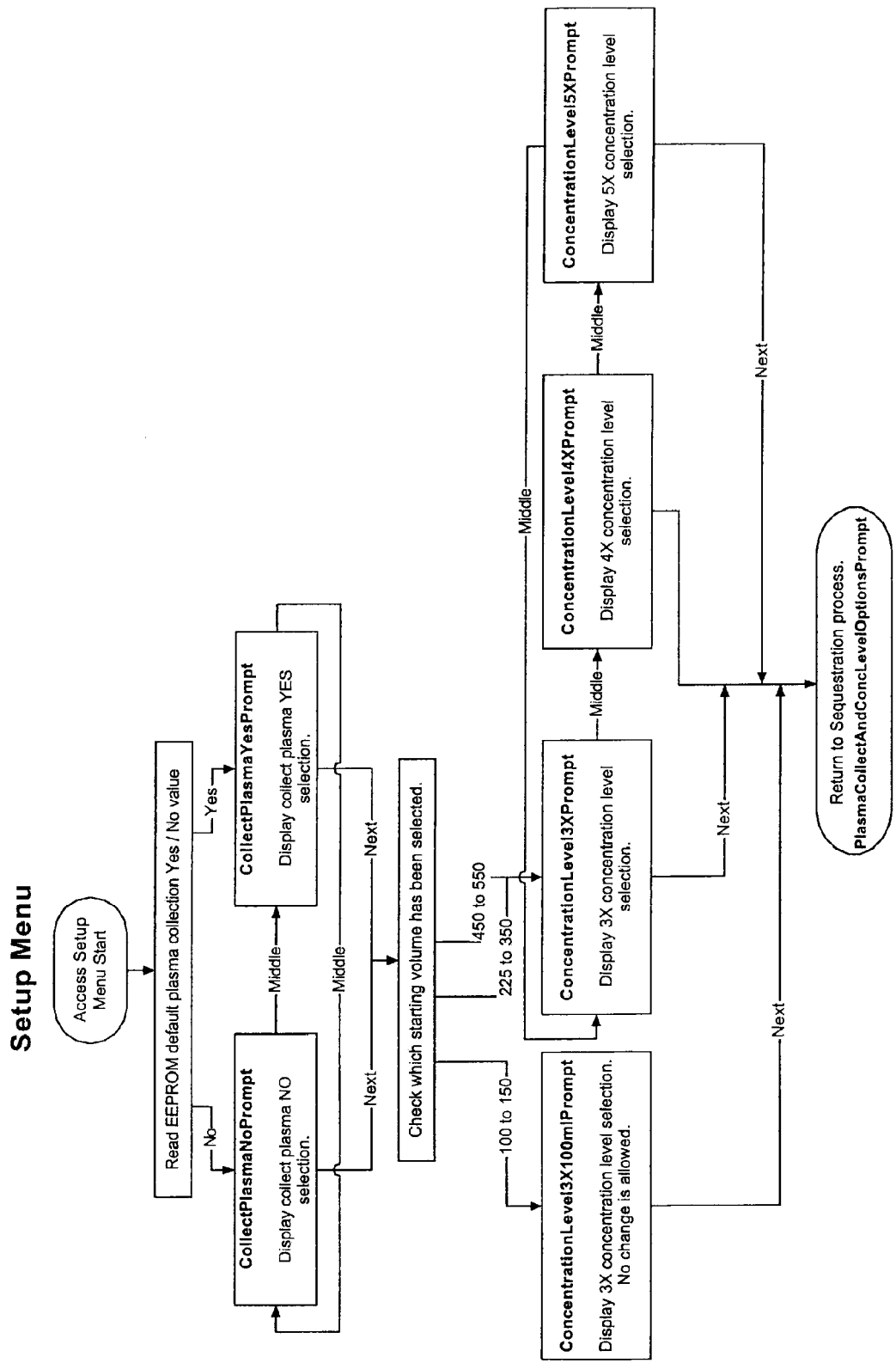
FIG. 7 is a schematic block flow diagram of an exemplary software design for apparatus setup options.
Figure 8:
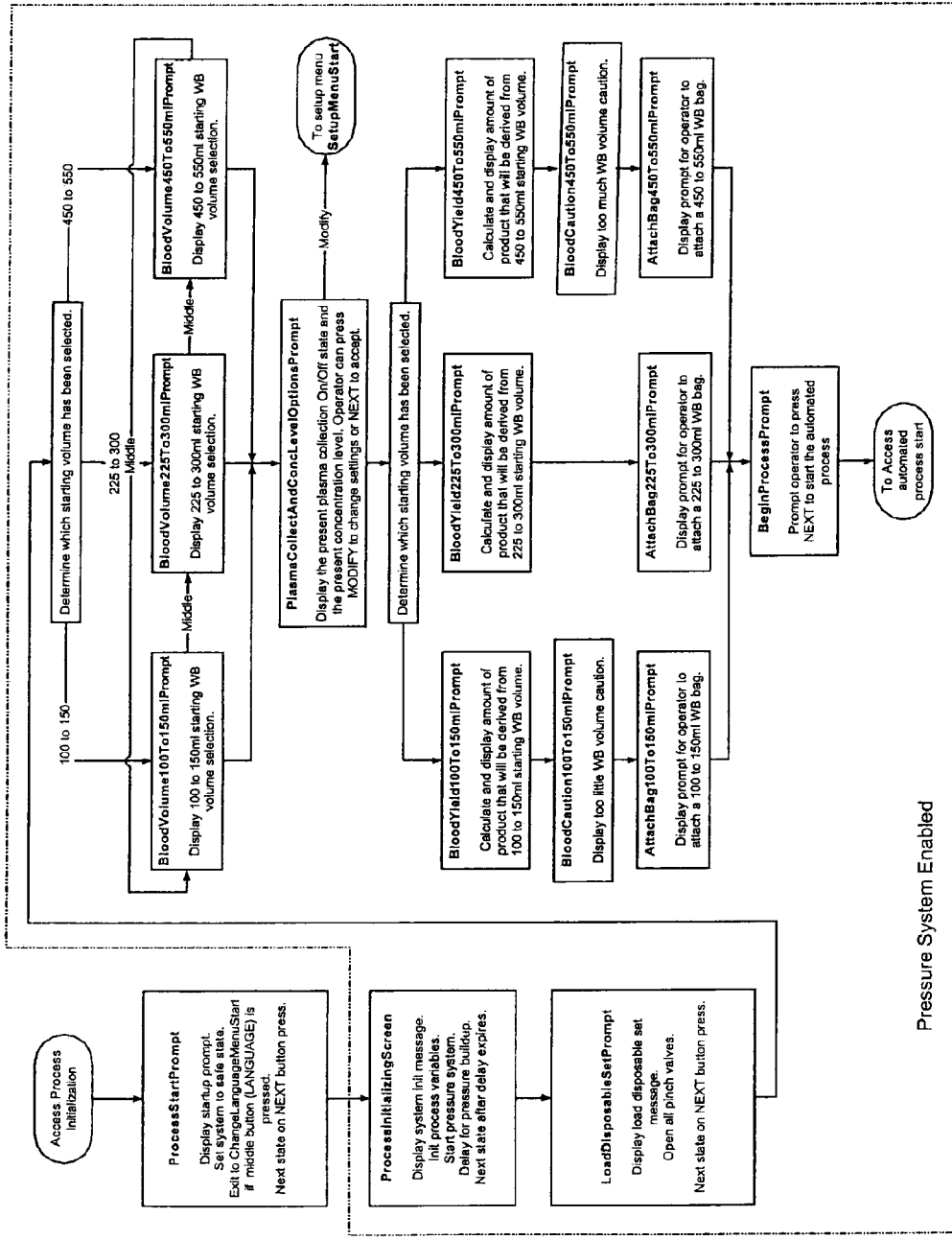
FIG. 8 is a schematic block flow diagram of an exemplary software design for apparatus initialization options and prompts.
Figure 9:
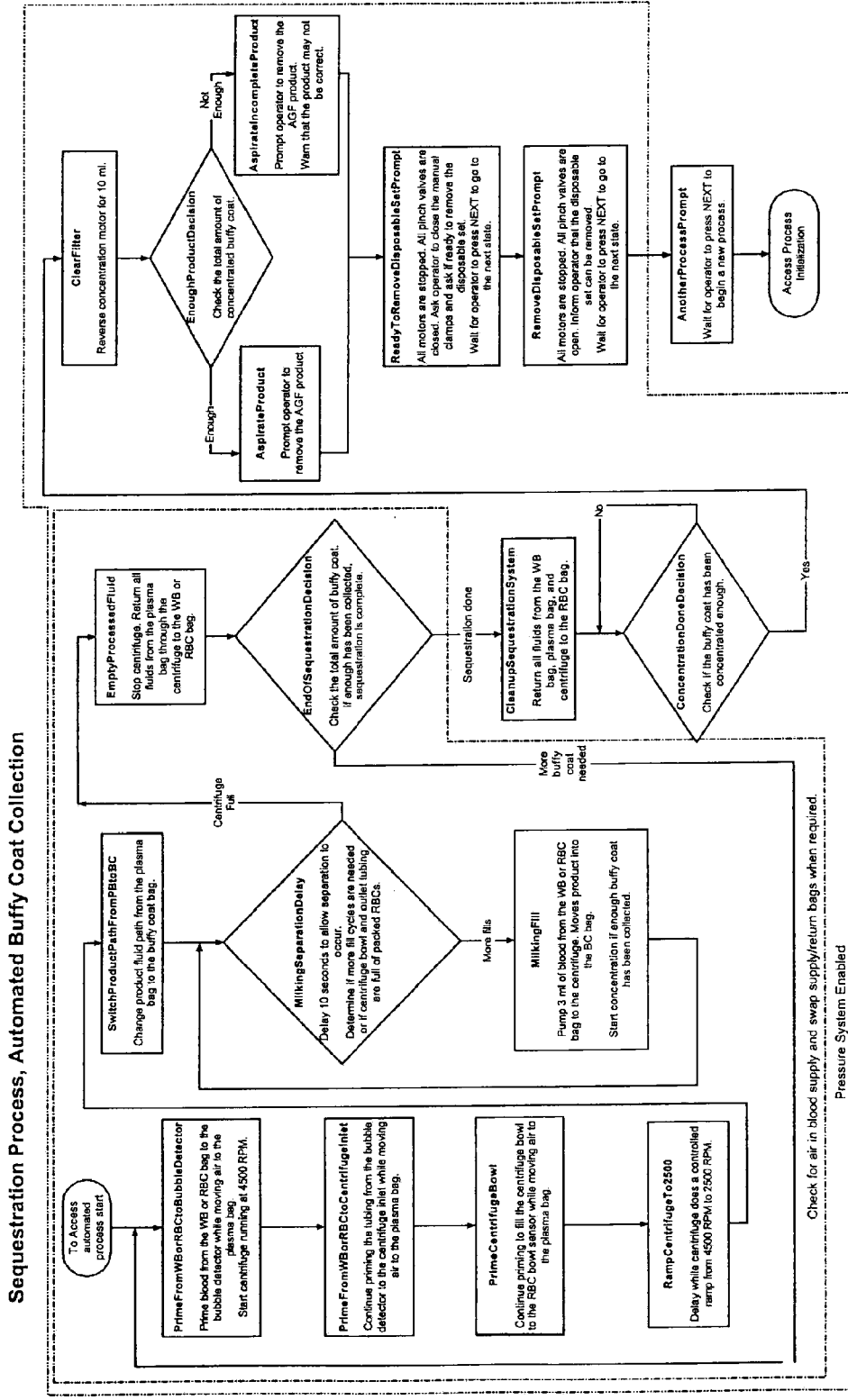
FIG. 9 is a schematic block flow diagram of an exemplary software design for automated buffy coat collection.
Figure 10:
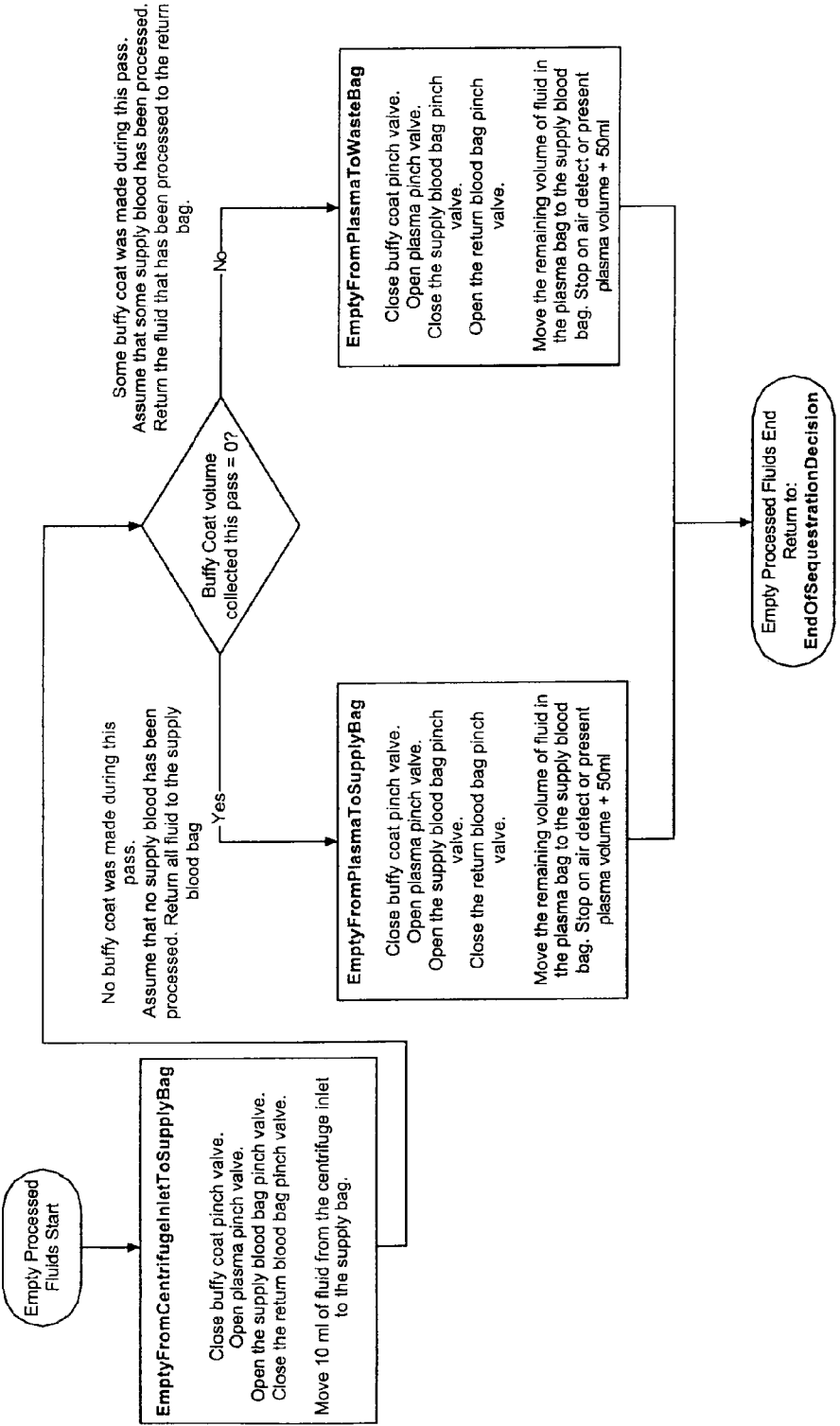
FIG. 10 is a schematic block flow diagram of an exemplary software design for automated emptying of process fluids into holding containers.
Figure 11:
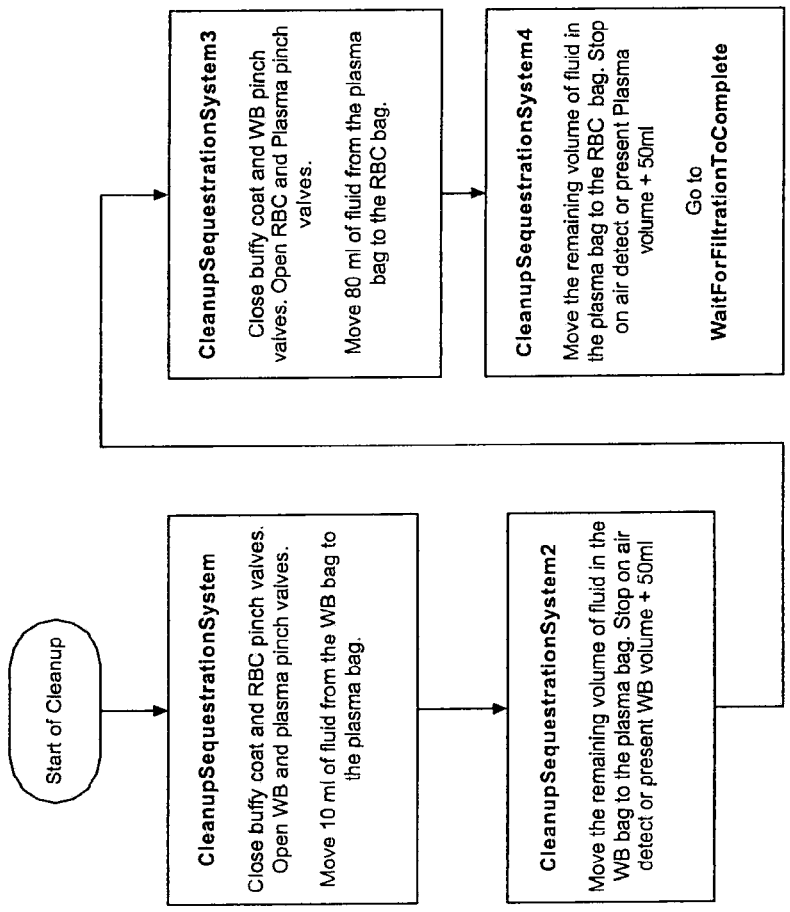
FIG. 11 is a schematic block flow diagram of an exemplary software design for an apparatus cleanup sequence.

FIG. 4 provides an exemplary block flow diagram of a software design to practice control system control of a process in the apparatus of the invention. The diagram suggests one of many possible schemes to provide a logical sequential flow of operator input, control system commands, and control system decisions to process variable load materials into a desired product, e.g., buffy coat. Embodiments of exemplary block flow diagrams for apparatus software are shown in FIGS. 5 to 11.

Operator Interface

The apparatus of the invention can have an interface for operator instructions to the control system. The operator can, e.g., input the volume of whole blood loaded into the apparatus or request the separated component be concentrated a desired amount. The operator interface can be configured, e.g., as a soft touch pad with arrows to navigate through a logical flow of menu options presented on an adjacent liquid crystal screen.

The apparatus can be designed with a control system capable of receiving basic operator input to start a separation/concentration process which can then be completed without additional actions by the operator. For example, after the operator inputs a load volume and a desired concentration factor, the apparatus can employ sensors, e.g., air sensors, level detectors, volume monitors and RBC detectors, and employ system controls, e.g., pump controls, valve controls and speed controls, to consistently provide desired product without further operator input.

The operator interface of the invention can also have, e.g., a control system output to provide operational options or to inform the operator of system conditions. The interface can display operator options, e.g., load volume choices, product concentration choices, selections for component composition, reprocessing options, and the like. The interface can display operator information, e.g., operator prompts, disc speed, current process status, notice of inconsistencies between operator inputs and process results, process completion notices, alarm conditions, etc.

Figure 12:
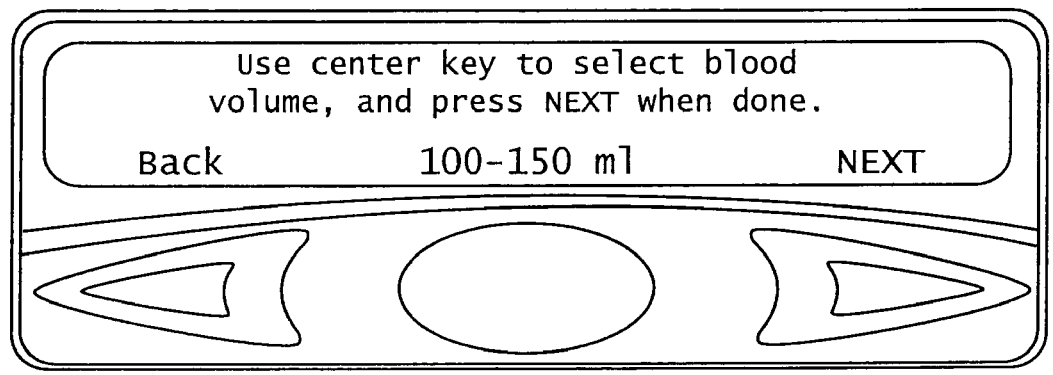
FIG. 12 is a schematic diagram of a flat panel liquid crystal display (LCD) and an operator interface touch pad.

The operator can interact with the control system through the operator interface to complete a desired separation and concentration process. For example, a flat panel liquid crystal display (LCD) can provide information to the user, and a 3-position (left, right, center) touch pad can provide responsive user inputs to the control system (see, FIG. 12). The right touch pad position can be an arrow, commonly below the word "NEXT" on the display, for the operator to press on completion of a task and/or to move on the next step. The word "BACK" can commonly be displayed over a left arrow on the touch pad for the operator to return to previous steps. The central touch pad position (center key) can be pressed by the operator, e.g., to toggle through numeric and/or logical options, presented in the center of the display, e.g., for setting of system parameters. For example, general operation of an exemplary apparatus of the invention can proceed as follows:

1) After the apparatus is powered up, a start up/self-check display informs the user to wait.
2) A prompt: "Load disposable kit. Press NEXT when done.", appears after the system self check. The user can press the right arrow (NEXT) after loading a disposable kit, to continue to the next prompt. Alternately, the user can press a center key, on the touch pad below the word "SETUP", to access a setup menu.
3) A prompt: "Use center key to select blood volume, and press Next when done.", appears after the operator presses the right arrow. A blood volume range, e.g., "450-500 ml" is presented in the center of the display. The user can press the right arrow (NEXT) if 450 to 500 ml of blood is to be processed. Alternately, the user can press the center key to cycle through alternate blood volume load ranges before selecting the appropriate range by pressing the right arrow (NEXT).
4) A prompt: "Plasma Collection. [###]. Processing Mode: [##]. Press NEXT to confirm settings.", appears after the operator presses the right arrow. The operator can press the center key to toggle through optional plasma collection or concentration settings. The operator can press the right arrow (NEXT) to confirm the settings and proceed.
5) A prompt: "450-500 ml of blood will yield 50-60 ml of product. Press NEXT to confirm.", appears after the operator presses the right arrow. The operator presses the right arrow (NEXT) to confirm or presses the left arrow (BACK) to return to the settings display.
6) A prompt: "Do you wish to collect plasma? Use center key to select option, then press NEXT.", appears after the operator presses the right arrow. The operator presses the center key to present a "YES" or "NO" before pressing the right arrow (NEXT) to select and proceed. If "YES" is selected, the apparatus will pause after an initial processing cycle (pass) is complete for the operator to collect some plasma from a plasma holding container.
7) A prompt: "Use center key to select processing mode, then press NEXT.", appears after the operator presses the right arrow. The operator can press the center key to present "NORMAL" or "SPLIT" processing options before proceeding by pressing the right arrow (NEXT). If "SPLIT" is selected, the apparatus will separate and concentrate a small volume of the total blood initially, allow the user to remove the initial concentrated plasma fraction, and then continue with the remainder of the operation.
8) A prompt: "Press NEXT to begin processing.", appears after the operator presses the right arrow. The operator presses the right arrow (NEXT) to proceed.
9) After the operator presses the right arrow, the process begins. A process status display appears continuously, e.g., indicating the volume processed, the volume of product, and/or the processing time.
10) If the operator chose to collect plasma at step 6, a prompt: "Plasma collection complete. Aspirate plasma, then press NEXT.", appears after completion of the first separation pass. The operator can press the right arrow (NEXT) to proceed after collecting the plasma sample.
11) A prompt: "Processing complete. Aspirate ## ml of product, then press NEXT.", appears after the operator presses the right arrow and the process is complete. The operator presses the right arrow (NEXT) to proceed after collecting concentrated plasma product.
12) A prompt: "Close holding bag clamps and detach bag if desired. Press UNLOAD to remove disposables.", appears after the operator presses the right arrow. The operator presses the right arrow (UNLOAD) to proceed before removing the disposable kit.
13) A prompt: "Please remove disposables. When finished, press done.", appears after the operator presses the right arrow. The operator presses the right arrow (DONE) to proceed after removing the disposable kit.
14) A prompt: "Ready to start new process. Press NEXT to continue.", appears after the operator presses the right arrow.

The foregoing operator interface sequence was offered to illustrate, but not to limit the claimed invention.

Detectors and Actuators

Much of the data acquisition by the control system of the invention has to do with process monitoring. For example, data can be acquired from one or more air detectors, pump turn counters, RBC level detectors, disc speed detectors, conduit RBC detectors, fluid level detectors, and/or the like.

The controller system of the invention can direct commands through an interface to provide hands free preparation of separated component concentrates. The control system can, e.g., direct pumps to transfer components, direct rotation of the separation disc, direct switching of valves to collect various components into various containers, and/or actuate the ultraconcentrator vacuum pump.

Detection of Flow Volumes

The control system can receive data from a sender at a pump to monitor the volume of fluids being transferred in the apparatus. The control system can, e.g., receive data input from a turn counter on the pump delivering load material to the separation disc. By monitoring the pump turns, the control system can determine, e.g., the amount of whole blood delivered to the separation disc or the amount of separated components pushed from the disc into the concentrator. Other ways to monitor transfer volumes will be apparent to those skilled in the art, such as measuring container weight, pump stroke counters, sonic/Doppler flow sensors, hydraulic motors, etc.

Air Detection

An air detector can be provided in the invention to detect when one or more containers or conduits are empty. Typically, an air sensor is operatively coupled to the first conduit between the whole blood load container and/or the RBC holding container and the separation disc. This configuration allows detection of the end of load material. When the air detector is triggered at the end of loading, the control system can, e.g., calculate the volume of whole blood loaded to the separation disc, switch a valve to continue loading from the RBC holding container and/or issue an alarm to the operator.

Air detectors can operate on a variety of principles known to those in the art. For example, the air detector can be operatively coupled to the conduit to detect air by changes in light absorbance, capacitance, conductivity, and the like.

RBC Level Detectors

The control system of the invention can receive data from an RBC level detector at the separation disc, e.g., to determine when it is time to collect buffy coat material. The RBC level detector can be of various designs readily appreciated by those skilled in the art. For example, an RBC detector can detect light absorbance, light scattering, fluorescence, etc.

The RBC level detector can be mounted (in operative orientation) on the apparatus and directed to monitor one or more predetermined levels within a transparent separation disc, or disc with a transparent window. As blood is loaded into the spinning separation disc, it can be separated into plasma and cells. The RBC detector can be configured to not trigger in the presence of the transparent amber plasma. However, as RBCs accumulate at the periphery of the continuously loaded separation disc, an RBC interface can eventually rise to a predetermined level and trigger the RBC level detector. The control system can respond to the triggered RBC level detector, e.g., by switching a valve to begin collection of buffy coat and start monitoring of the buffy coat volume collected.

The level of RBCs in the separation disc that will trigger the RBC level detector can be set, e.g., as a start or end point for collection of a blood component. For example, the RBC detection level can be set near the top of the separation disc to trip shortly before RBCs exit the outlet port as a signal to end collection of plasma and start collection of buffy coat. Alternately, e.g., the RBC detection level can be set lower to end collection of platelet poor plasma and to start the collection of a plasma-buffy coat rich in platelets.

The RBC detector level can be adjusted to suit the particular volume, geometry and rotation speed of the separation disc. The level can be determined empirically or it can be predicted by calculations, e.g., involving disc volumes, desired component characteristics, dead volumes, and the like, as would be appreciated by those skilled in the art. The apparatus of the invention can have multiple or movable RBC level detectors to provide a choice of detection levels.

The RBC detector can be configured in ways apparent to those skilled in the art to be triggered by cell interfaces other than RBC interfaces. The RBC detector can be configured to trigger on detection of, e.g., platelets, WBCs, bone marrow cells, disaggregated tissue cells, cultured cells, homogenized glandular organ cells, and the like.

Separation Disc Speed

Separation disc speed can be received by the control system as input, e.g., to confirm the disc is at a speed appropriate for loading or milking, as feedback in a speed control loop, or for safety monitoring. In one embodiment of the invention, blood is not loaded into the disc until a predetermined speed is reached, e.g., 4500 rpm (approximately 2000×g). In another embodiment, the control system does not initiate collection (milking) of buffy coat until the separation disc has slowed to, e.g., 2000 rpm (or approximately 500 to 1000×g). The control system can also monitor separation disc speed for safety considerations, e.g., to alarm or shut down in an over speed situation or to maintain a door lock until the disc stops spinning at the end of a process.

Speed detection of the separation disc can be by any method known in the art. The disc rotation speed can be determined by, e.g., an optical sensor directed at the disc, a mechanical turn counter, an electronic impulse counter in the drive motor power circuit, and/or the like.

In one aspect of the invention, the control system controls the speed of the separation disc. The control system can, e.g., receive data input from any of the disc speed detectors described above and can continuously adjust the speed through feedback mechanisms known in the art.

Conduit RBC Detector

The apparatus of the invention can employ an RBC detector, e.g., on the second conduit between the separation disc and the concentrator, to precisely detect the end of buffy coat flow from the separation disc. A signal from an RBC detector on the second conduit to the control system can, e.g., end collection of buffy coat, initiate calculation of buffy coat volume, and/or initiate pump reversal to empty RBCs from the separation disc.

As with the RBC level detector, a conduit RBC detector can be of various designs known in the art such as, light absorbance detectors, light scatter detectors, fluorescence detectors, etc. The sensitivity of the detector can be set to trigger at a particular concentration of RBCs, WBCs or other cells. The detector can send a quantitative signal to the control system, thus allowing reconfiguration of the trigger level as appropriate to, e.g., detect buffy coat, disaggregated tissue cells, or to change the amount of RBCs collected in a product stream.

Filtrate Volume Detector

The volume of a separated component concentrate can be measured directly, e.g., by determining the weight or fluid level of concentrate in the concentrate holding container. However, as variable amounts of concentrate can be in other loop components, the concentrate volume is typically measured indirectly as the separated component volume supplied minus the filtrate volume removed.

The filtrate volume can be detected by any number of methods in the art such as, container net weight, variable resistors coupled to floats, dip rod capacitors, etc. In one embodiment of the invention, filtrate volume is detected by placing an optical array across the path of a float to determine the level of fluid in the filtrate container. As the fluid level changes, the float shifts to block light transmission between a series of optical elements, e.g., LEDs and photodiodes, thus progressively changing the pattern of signals transmitted to the controller. The controller can be calibrated to translate optical array transmissions into actual filtrate volumes.

The control system can be programmed to respond to filtrate volume data, e.g., by stopping the second pump operatively coupled to the recirculating concentration loop to end concentration of product and/or by reversing the pump to purge concentrate from the concentrator and conduit back into the concentrate holding (second) container.

Pump Control

The control system of the invention can control transfer of fluids in the apparatus by pump control commands through an interface. The control system can control the first pump operatively coupled to the first conduit, e.g., to start a separation by pumping blood from a whole blood (first) container into the separation disc, intermittently pump additional blood to milk a buffy coat collection after the RBC level is detected, reverse flow to empty packed depleted RBCs from the disc to an RBC holding container, etc.

The control system can control the second pump on a recirculating concentration loop to, e.g., start recirculation when sufficient separated product has been collected in the concentrate holding (second) container or reverse flow at the end of concentration to collect the loop dead-volume back into the holding container.

Valve Control

The control system of the invention can optionally employ valves to direct the flow of, e.g., blood or components being transferred by the pumps of the apparatus.

A variety of valves, known in the art, can be used to provide the valve control functions of the invention. Fluid control valve configurations range from, e.g., diaphragm, ball and seat, rotary, pinch, washer and seat, needle and jet, flap, etc. Valves can be one way, two way, junction (T) valves, spider valves, etc. Computer control of valves is often carried out through an interface to actuate a solenoid or motor to directly switch a valve. Alternately, e.g., a computer controlled solenoid can open an air valve which releases pressurized air to actuate a pneumatic valve which ultimately controls fluid flow.

Valves of the present invention are typically sanitary types switched through electrical or pneumatic force. For example, a pneumatic pinch valve with two working positions can alternately allow flow to or from two containers connected to the same conduit. Such a flow path is useful in the invention, e.g., to load whole blood from the first container through the first conduit then allow return of depleted RBCs, through the same conduit, to the RBC holding container by simply switching the valve and reversing the first pump.

Pinch style valves are well adapted to the present invention for their sanitary properties and disposability. Automated pinch valves can be actuated by solenoids or pneumatic actuators to squeeze conduits, e.g., peristaltic tubing, of the invention, thus controlling flow. Blood or components within the tubing do not come in contact with mechanical parts and the tubing can be part of an aseptically sealed disposable set.

Control System Calculations

The apparatus of the invention can provide consistent hands free operations with flexible responses to variable circumstances. The apparatus can accomplish this by using the detectors and control commands (described above) in combination with calculations and programmed logic.

In one embodiment, the apparatus determines a blood volume ($V_b$) transferred to the separation disc by monitoring a turn counter on the first pump. For example, a particular peristaltic pump using a particular type of peristaltic tubing can deliver a consistent volume of fluid with every turn of the pump. The control system can monitor a load turn count from the beginning of separation disc loading to the trigger of the air detector. The control system can calculate the blood volume ($V_b$) transferred by multiplying the load turn count by a known, e.g., empirically derived, delivery volume per turn.

In a similar fashion, a separated component volume ($V_{sc}$) can be calculated. The control system can calculate component volume by monitoring a collection or milking turn count from the beginning of collection of a separated component to the end of collection. For example, a buffy coat volume can be calculated by starting a turn count when the RBC level detector triggers and a valve opens to collect buffy coat in the second container. The turn count continues until RBCs exit the separation disc to trigger the outlet RBC detector stopping the pump. In this example, the control system can calculate buffy coat volume from the turn count between the trigger of the RBC level detector and the trigger of the outlet RBC detector. If the apparatus continues to process additional blood loads in additional passes of blood separation, the control system can calculate the total buffy coat volume collected from the sum total turn counts between triggering events of each pass.

Although the volume of concentrated separated components ($V_{csc}$) can be measured directly, one aspect of the invention provides a way to calculate the volume of concentrated components ($V_{csc}$) by subtracting the filtrate volume ($V_f$) from the separated component volume ($V_{sc}$). As separated components are concentrated, part of their volume is lost as filtrate on the permeate side to the ultrafiltration membrane. Still, the volume of the concentrated separated component ($V_{csc}$) plus the volume of the filtrate ($V_f$) must equal the original volume of the separated component ($V_{sc}$). Therefore, the volume of the concentrated separated component ($V_{csc}$) must equal the original volume of the separated component ($V_{sc}$) minus the volume of the filtrate ($V_f$). That is:

If $V_{csc} + V_f = V_{sc}$, then $V_{csc} = V_{sc} - V_f$.

In this aspect of the invention, the separated component volume ($V_{sc}$) is known, e.g., from pump turn counts and the filtrate volume ($V_f$) is known, e.g., from optic array monitoring at the filtrate container. A simple arithmetic calculation by the control system can therefrom provide the concentrated separated component volume ($V_{csc}$).

Another aspect of the invention can be a check system to receive the operator's expectations and then to determine whether the process went as expected. At the start of a process, the operator can be prompted to input, e.g., an expected blood volume ($V_{eb}$) of load material. At the end of loading, the actual blood volume ($V_b$) is known from control system monitoring of the pump turn counts. It is a simple calculation for the control system to compare the expected and actual volumes to confirm the process went as expected. Should the values differ by a predetermined amount, e.g., about 30% or more, the control system can issue a notice to the operator presenting the difference and the potential consequences to products of the system.

The control system can calculate an expected separated component volume ($V_{esc}$) from the blood volume ($V_b$) times a separation factor. The separation factor is the portion of load that will be removed into the separated component. The separation factor can, e.g., be input by the operator or reside as a default setting in the control system. The apparatus will continue processing until the actual separated component volume ($V_{sc}$) equals the expected separated component volume ($V_{esc}$). For example, if the blood volume ($V_b$) loaded to the apparatus is 500 ml and the separation factor is 0.30, then the apparatus will continue processing until 150 ml of separated component has been collected. Typical separation factors for separation of blood components by the apparatus range from about 0.25 to about 0.4. (Note: A table can be provided to the operator to calculate, e.g., an expected buffy coat volume taking into account both the overall blood volume and the hematocrit. The hematocrit can be determined, e.g., from the volume of blood it takes to complete the first pass to the point of RBC detection.)

The control system can calculate an expected concentrated separated component volume ($V_{ecsc}$) from the separated component volume ($V_{sc}$), times a concentration factor. The concentration factor is the portion of separated component that will be retained on the retentate side of the ultrafiltration membrane during concentration. The concentration factor can, e.g., be input by the operator or reside as a default setting in the control system. The apparatus can continue concentration until the actual concentrated separated component volume ($V_{csc}$) equals the expected concentrated separated component volume ($V_{ecsc}$). For example, if the separated component volume ($V_{sc}$) collected by the apparatus is 150 ml and the concentration factor is 0.33, then the apparatus will continue concentration until, e.g., 50 ml of concentrated separated component remains in the recirculating concentrator loop (100 ml of filtrate detected in the filtrate container). Typical concentration factors for concentration of separated blood components by the apparatus range from about 0.20 to about 0.4 or about 0.33.

In another embodiment of the invention, the operator can optionally pause processing before completion of processing by manual intervention or by programming through the operator interface. For example, the separation and/or concentration operations can be split to an early and final phase, separated by a pause to allow early sampling of certain blood components. Early sampled components can include, e.g., plasma before concentration.

Plasma-Buffy Coat Concentrates

The apparatus of the present invention provides flexible control systems, e.g., to consistently produce concentrated platelet free plasma for a fibrin glue or plasma-buffy coat concentrates for wound seal/tissue regrowth matrices.

Concentrated plasma alone can act as a fibrin glue when exposed to and activator in the presence of calcium ions. Unconcentrated plasma contains fibrinogen at levels of about 2-4 mg/ml. For consistent, reliable gelling in a fibrin glue composition, useful levels of fibrinogen are about, e.g., 5 mg/ml or more. Therefore, plasma is concentrated, e.g., about 2.5-fold or more for preparation of a fibrin glue. Fibrinogen levels are often below normal in ill patients, thus requiring further concentration of autologous plasma from these patients for fibrin glue preparations.

Fibrinogen protein is cut by thrombin in the presence of calcium ions to produce an insoluble fibrin network. The coagulation time and strength of a fibrin glue depends on the concentrations of fibrinogen, calcium ions and thrombin. Thrombin and calcium are added to a fibrinogen concentrate just before application of the fibrin glue to seal a wound. Fibrinogen concentrations of at least about, e.g., 5 mg/ml, are provided in the invention by ultrafiltration concentration of plasma. Thrombin is added at about 100 U/ml or more, with lesser amounts slowing clot formation. Calcium ions can be added to the fibrin glue preparation in amounts adequate to overwhelm any calcium chelating anticoagulant plus, e.g., 0.004 mg $Ca^{++}$ per unit of thrombin. Plasma concentrates also provide other coagulation proteins, such as factor XIII which promote polymerization or cross linking of the fibrin.

The plasma-buffy coat composition of the invention includes, e.g., concentrated fibrinogen, concentrated platelets, and/or concentrated white cells. Each of these elements can provide benefits for a wound sealant or tissue regrowth matrix.

The platelet count of normal whole blood is about 150,000 to 400,000 per microliter. In a buffy coat concentrate, platelets are concentrated to, e.g., at least about $1 \times 10^6$ per microliter, or approximately 6 to 10-fold. In the present invention, this can be accomplished through a combination centrifugal concentration and ultrafiltration. The enhanced platelet concentration in a buffy coat concentrate can provide a strong contracting matrix. In addition, platelets can release growth factors, e.g., PDGF, that promote healing.

Normal WBC counts in peripheral blood are, e.g., 4,000 to 11,000 cells per microliter. WBCs number, e.g., at least about 20,000 per microliter, in a buffy coat concentrate. As with platelets, in the present invention, WBCs are concentrated through a combination of centrifugal concentration and ultrafiltration. The large number of WBCs in buffy coat concentrate provides a mix of growth factors and possible infection fighting capabilities. Buffy coat concentrates prepared by the methods or in the apparatus of the invention can provide white cells concentrated 4 fold, 8-fold, or more.

Additional structural elements can be added to a buffy coat concentrate to provide scaffolding for regrowth of damaged tissues. For example, ground autologous bone can be mixed into buffy coat concentrate to prepare a bone growth matrix. Such a matrix can be, e.g., used to fill surgical drill holes or poorly contacting bone fractures.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus to produce concentrated blood components, which apparatus comprises:
   a) a separation disc which receives blood through a first conduit, which separation disc rotates to generate centripetal force, thereby separating the blood into two or more blood components according to density;
   b) a control system operably connected to a first pump operably coupled to the first conduit, wherein the control system controls transfer of blood and/or blood components to the separation disc by controlling the pump; and, c) a concentrator which receives one or more of the blood components from the separation disc through a second conduit, which concentrator comprises at least one ultrafiltration membrane, which membrane comprises a retentate side and a permeate side wherein, during operation of the apparatus, the blood components being contacted to the retentate side of the membrane with a pressure gradient, thereby forcing one or more low molecular weight molecules through the membrane to a permeate side of the membrane and concentrating blood components.

* * * * *